US009968510B2

(12) United States Patent
Liu

(10) Patent No.: US 9,968,510 B2
(45) Date of Patent: May 15, 2018

(54) INTELLIGENT INTRAOCULAR AND EXTRAOCULAR MUSCLE SENSITIVE EXERCISE TRAINING INSTRUMENT AND TRAINING METHOD

(71) Applicant: Dongguang Liu, Guangdong (CN)

(72) Inventor: Dongguang Liu, Guangdong (CN)

( * ) Notice: Subject to any disclaimer, the term of this patent is extended or adjusted under 35 U.S.C. 154(b) by 0 days. days.

(21) Appl. No.: 15/312,664

(22) PCT Filed: Dec. 25, 2015

(86) PCT No.: PCT/CN2015/099018
§ 371 (c)(1),
(2) Date: Nov. 21, 2016

(87) PCT Pub. No.: WO2017/080054
PCT Pub. Date: May 18, 2017

(65) Prior Publication Data
US 2017/0281454 A1 Oct. 5, 2017

(30) Foreign Application Priority Data
Nov. 11, 2015 (CN) ......................... 2015 1 0768408

(51) Int. Cl.
*A61B 3/00* (2006.01)
*A61H 5/00* (2006.01)
*A63B 23/025* (2006.01)
*A63B 24/00* (2006.01)

(52) U.S. Cl.
CPC ............ *A61H 5/00* (2013.01); *A63B 23/025* (2013.01); *A63B 24/0087* (2013.01); *A61H 2201/0157* (2013.01); *A61H 2201/0188* (2013.01); *A63B 2207/02* (2013.01)

(58) Field of Classification Search
CPC .... A63B 23/025; A63B 24/0087; A61H 5/00; A61B 3/032; A61B 3/00; A61B 3/02; A61B 3/08
USPC ........................................ 351/200, 203, 246
See application file for complete search history.

(56) References Cited

U.S. PATENT DOCUMENTS

2012/0330415 A1* 12/2012 Callahan .............. A61F 2/1694 623/6.43

FOREIGN PATENT DOCUMENTS

FR 2847682 A1 * 5/2004 ............ G02C 5/001
JP 2002238962 A * 8/2002

* cited by examiner

*Primary Examiner* — James Greece

(57) ABSTRACT

An intelligent intraocular and extraocular muscle sensitivity exercise training instrument which is disposed with an ocular head (1) consisting of a front shell (11), a middle shell (12) and a back shell (13), and a control device (2) electrically connected to the ocular head (1), as well as an intraocular muscle exercise bar (3) electrically connected to the control device (2). The beneficial effects are as below: in addition to supplementing the field of portable intraocular and extraocular muscle training instruments, it is also convenient for students to put it in their school bags for use at any time thanks to its intelligent operations and foldable structure, it overcomes the shortcomings of the above-mentioned pure extraocular and intraocular muscle sensitivity training instruments. Therefore, it is bound to have a profound effect on myopia control, dyslexia remediation, eye healthcare, and memory improvement among teenagers.

10 Claims, 8 Drawing Sheets

INTELLIGENT INTRAOCULAR AND EXTRAOCULAR MUSCLE SENSITIVE EXERCISE TRAINING INSTRUMENT AND TRAINING METHOD

BACKGROUND OF THE INVENTION

The present invention relates to the field of medical devices in eye treatment, and more specifically, to a portable and intelligent intraocular and extraocular muscle sensitive exercise training instrument and its training method.

The intraocular muscle or ciliaris sensitivity exercise (i.e., sensitivity adjustment training) can help prevent and control myopia, mitigate presbyopia, prevent and treat eye fatigue and improve low vision of amblyopia, and also can remedy dyslexia and ADHD among children and so on. However, no major progress in instrument R&D was made over the past 30 years.

Currently, the intraocular muscle training and sensitivity exercise adjustment instruments in the Chinese market mainly include flip glasses and a linear training instrument. They are mainly provided with the following functions:

The flip glasses use positive and negative lenses which take turns to turn over for sensitivity training and adjustment. To prevent dizziness, eye distension and blurred vision, the degree of the positive and negative lenses is usually limited to less than 2.5D. Namely, the training is less forceful. In addition, users need to constantly turn over the lenses by hands, so it is very inconvenient to use and has poor compliance. A few months ago, I (Liu Dongguang) invented automated flip glasses, which still have the certain limitation of less forceful adjustment and training intensity in such products, despite some advantages.

The linear training instrument is known domestically as a kind of large-sized instrument mainly used in hospitals and training centers, with several thousand to tens of thousands yuan in price. China has a shortage of intelligent linear training instruments for family use. On the other hand, small-sized linear training instruments for family use produced in foreign countries have some shortcomings, for example, they cannot being folded to become smaller due to their longer bodies (about 1M), so they are inconvenient for users, especially teenagers, to take along, and additionally they are all sold at prices of over 1,000 yuan. They are not good for the promotion among adolescent students.

Furthermore, related studies show that the lateral rectus (six pieces) sensitivity exercise is not only beneficial to eye healthcare and dyslexia remediation, but also can strengthen memory so as to improve intelligence. It has a profound effect on improving the quality of human eye healthcare.

The domestic patent of a vision device (Patent No. 95115473.7) discloses a technical solution of amblyopia treatment, which uses the principle of casing pipe to make a sighting mark connecting rod, and then ask patients to gaze at lighting sighting marks disposed at the end of the sighting mark connecting rod, so as to treat patients with amblyopia. However, the structure of the technical solution may bring many inconveniences; for example, patients need to adjust the distance of the sighting marks by manually adjusting the sighting mark connecting rod, but in reality, it needs to constantly or intermittently adjust the distance between the sighting marks and patients' eyes during the entire training process, so the technical solution is not suitable for long-time use; moreover, as the sighting mark connecting rod of the technical solution adopts a casing pipe mechanism which cannot be removed, so that it is inconvenient to take along due to a relatively large volume.

Based on the above-mentioned contents as well as reviews of domestic and foreign literature, it is found that there are no instruments provided with both intraocular and extraocular muscle sensitivity exercise training functions. Therefore, it is necessary to make up the blank and drawback of the prior art, thus to provide an intraocular and extraocular muscle sensitivity exercise training instrument which has a simple structure and is convenient to use and take along.

BRIEF SUMMARY OF THE INVENTION

In view of the deficiencies of the prior art, the present invention is intended to provide an intelligent intraocular and extraocular muscle sensitivity exercise training instrument and its training method, which realizes the assembly or separation of an ocular head, a control device and an intraocular muscle exercise bar by way of electrical insert connection, to save space to the greatest extent when taking it along; meanwhile, the intraocular muscle exercise bar is connected via the assembly of several intraocular muscle exercise bar components, so it can realize matching of various lengths according to different needs.

Furthermore, each intraocular muscle exercise bar component is provided with vertically arranged LED guiding color light sets, so that when the assembly of several intraocular muscle exercise bar components is completed, it can realize various flash cycle ways according to different training modes, taking LED guiding color lights or a set of lights as an unit; on the other hand, in order to realize the extraocular muscle training, an extraocular muscle exercise light panel is disposed in glasses frames of the ocular head as well, which can realize various flash modes along the periphery of eyes, thus to eventually realize intraocular and extraocular muscle trainings; what's more, diopter correcting lenses are also provided in the ocular head. Thanks to the structure mode and training method mentioned above, the following effects can be achieved: improving the intraocular and extraocular muscle coordinated exercise sensitivity, enhancing memory, remedying dyslexia and ADHD, and preventing and controlling myopia and improving low vision of amblyopia.

To achieve the purposes above, the present invention adopts the following technical solutions:

An intelligent intraocular and extraocular muscle sensitivity exercise training instrument which is disposed with an ocular head consisting of a front shell, a middle shell and a back shell, and a control device electrically connected to the ocular head, as well as an intraocular muscle exercise bar electrically connected to the control device;

wherein the control device comprises a drive power supply, a microprocessor, a training function selection module, a MP3 module and a buzzer: the microprocessor is in electrical connection with the drive power supply, as well as the training function selection module and the MP3 module respectively, and the buzzer is in electrical connection with the MP3 module;

the intraocular muscle exercise bar is connected via several intraocular muscle exercise bar components, the shell of which is composed of an upper cover and a lower cover of the intraocular muscle exercise bar, with an intraocular muscle exercise light panel disposed inside; the intraocular muscle exercise light panel is arranged with at least a set of LED guiding color lights on it, with its front and back ends disposed with an electrical connection port and an electrical connection socket respectively, and the several intraocular muscle exercise bar components are connected in turn via the electrical connection port or the electrical connection socket;

it also comprises diopter correcting lenses, as well as an extraocular muscle exercise light panel disposed with several LED guiding lights on it, in the ocular head.

It needs to be noted that, to prevent the disjunction of the several intraocular muscle exercise bar components in connection, the front end of the intraocular muscle exercise bar components is arranged with a groove, with its back end disposed with a flange matched with the groove; when the several intraocular muscle exercise bar components need to be assembled for using, the flange of the prior intraocular muscle exercise bar component is inserted into the groove of the posterior intraocular muscle exercise bar component, which not only realizes extension, but also enhances the stability of the connection between individual components.

As a preferable technical solution, it needs to be noted that, the intraocular muscle exercise bar consists of five to ten intraocular muscle exercise bar components, and each of the intraocular muscle exercise bar components is provided with two sets of vertically arranged LED guiding color lights with each set having three, wherein the colors of the LED guiding color lights include but are not limited to red, yellow or green light.

It needs to be further noted that the front end of the control device is disposed with the groove matched with the flange.

It needs to be further noted that positions of the several LED guiding lights arranged on the extraocular muscle exercise light panel shall be in correspondence with positions at the periphery of users' eyes; preferably, the number of the LED guiding lights is eight.

As a preferable technical solution, it needs to be noted that, both the electrical connection port and the electrical connection socket used between the ocular head and the control device and the intraocular muscle exercise bar components of the present invention are USB ports.

It needs to be further noted that, the back shell of the ocular head is also disposed with a fixing band designed for users to wear.

Based on the structure of the above-mentioned training instrument, the present invention also provides the following training method:

A method using the intelligent intraocular and extraocular muscle sensitivity exercise training instrument for training, and the training method comprises:

S1, insert the control device into the ocular head;

S2, keep the intraocular muscle exercise bar components in front-and-back insert connection to reach the length required by users;

S3, insert the completely connected intraocular muscle exercise bar into the control device, so that users can wear the ocular head onto their eyes;

S4, turn on the power supply, and use the control device to adjust the training function selection module according to different needs, so as to trigger the LED guiding color lights or the LED guiding lights arranged on the intraocular muscle exercise bar or the extraocular muscle exercise light panel to start, thus to realize various training modes;

S5, when the training is completed, execute reverse steps of S1-S3 to separate and collect the ocular head, the control device and the intraocular muscle exercise bar components.

It needs to be further noted that, the intraocular muscle training modes comprise:

"己"-shaped single LED guiding color light cycle mode: LED guiding color lights are lightened one-by-one transversely from the first one at the frontmost end, until the last LED guiding color light is lightened, then the lights continue to be lightened one-by-one along a vertical direction and repeat the cycle, and stop five minutes later when a buzzer sounds;

whole-set cycle mode: taking a set of LED guiding color lights as a unit, the light sets are lightened one-by-one from the first one at the frontmost end to the last one, then repeat the cycle, and stop five minutes later when a buzzer sounds;

"⊔⊓"-shaped single LED guiding color light cycle mode: LED guiding color lights are lightened one-by-one transversely from the first one at the frontmost end, then repeat the cycle, and stop five minutes later when a buzzer sounds;

mixed mode: the three modes mentioned above appear repeatedly, and stop five minutes later when a buzzer sounds.

It needs to be further noted that, the extraocular muscle training modes comprise:

Random cycle mode: LED guiding lights not adjacent to each other flash one-by-one cyclically by a random lightening way;

clockwise or anticlockwise cycle mode: LED guiding lights flash cyclically in a clockwise or anticlockwise direction;

flash mode: LED guiding lights at both left and right sides are lightened simultaneously and flash cyclically.

The beneficial effects of the present invention are as below:

supplementing the field of portable intraocular and extraocular muscle training instruments, being convenient for students to put it in their school bags for using at any time with its intelligent operation and foldable structure, and overcoming the shortcomings of the above-mentioned pure extraocular and intraocular muscle sensitivity training instruments. Therefore, it is bound to have a profound effect on myopia control, dyslexia remediation, eye healthcare, and memory improvement among teenagers.

Figure 1:
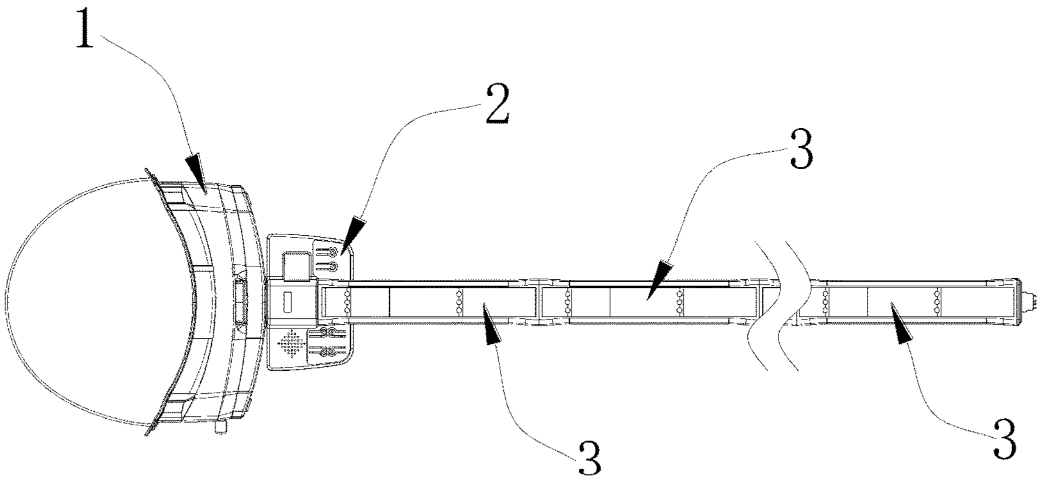
FIG. 1 is an overall structural diagram of the present invention.

Marks in Figures: ocular head 1, ocular head's front shell 11, middle shell 12 and back shell 13, diopter correcting lenses 14, control device 2, control device's upper cover 21, control device's lower cover 22, PCB panel 23, drive power supply 24, microprocessor 25, training function selection module 26, MP3 module 27, buzzer 28, intraocular muscle exercise bar components 3, intraocular muscle exercise bar's upper cover 31 and lower cover 32, intraocular muscle exercise light panel 33, LED guiding color light 34, groove 35, flange 36, electrical-connection port 100, electrical connection socket 101, extraocular muscle exercise light panel 4, LED guiding light 41, fixing band 200.

DETAILED DESCRIPTION OF THE INVENTION

The present invention is further detailed in combination with the Figures as follows. It needs to be noted that the embodiment gives detailed modes of execution and processes of operation on the premise of the technical solution, but the protective scope of the invention is not limited to the embodiment.

Figure 5:
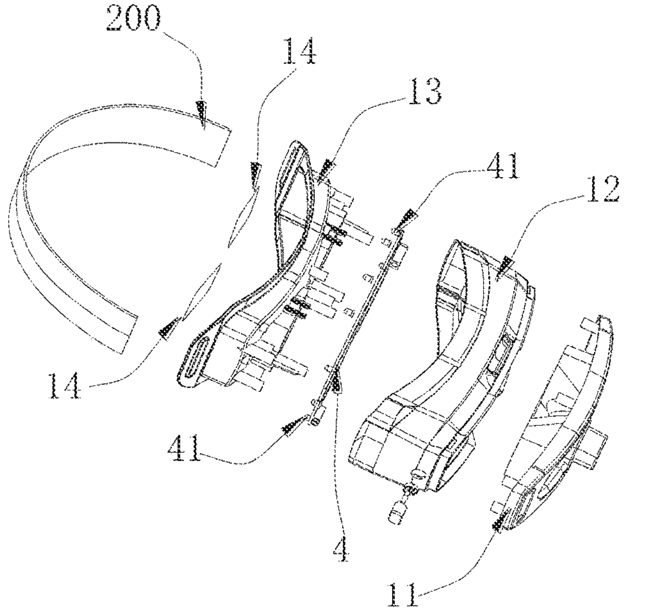
FIG. 5 is a structural diagram of the extraocular muscle exercise light panel of the present invention.

As shown in FIG. 1 and FIG. 5, the present invention is an intelligent intraocular and extraocular muscle sensitivity exercise training instrument which is disposed with an ocular head 1 consisting of a front shell 11, a middle shell 12 and a back shell 13, and a control device 2 electrically connected to the ocular head 1, as well as an intraocular muscle exercise bar electrically connected to the control device 2.

Figure 2:
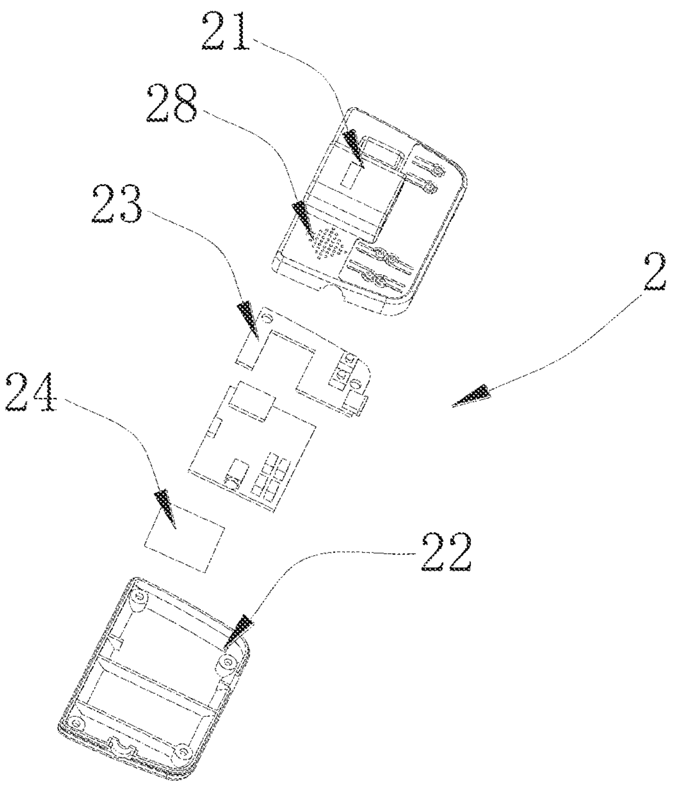
FIG. 2 is a structural diagram of the control device shown in FIG. 1.
Figure 3:
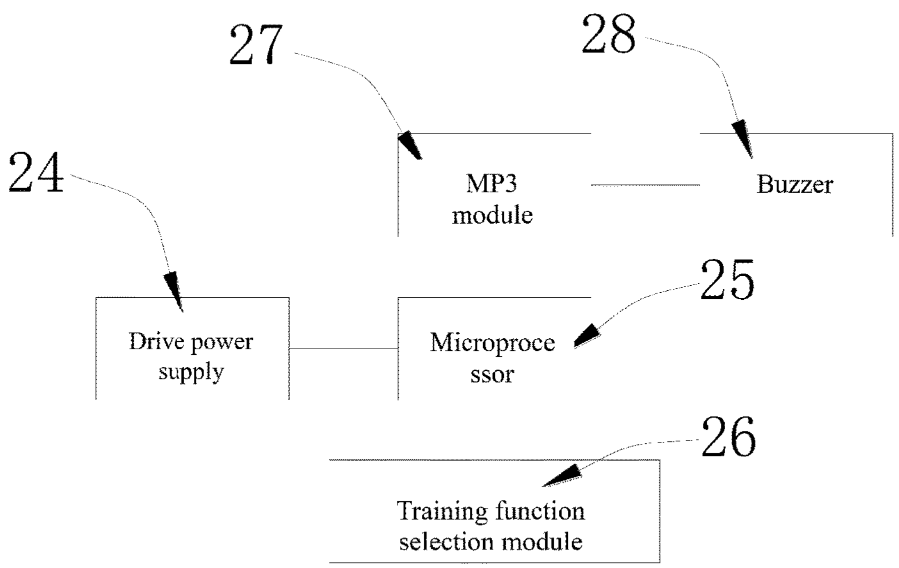
FIG. 3 is a connection diagram of all modules of the control device shown in FIG. 2.

As shown in FIG. 2 and FIG. 3, consisting of its upper cover 21 and its lower cover 22, the shell of the control device 2 is disposed with a controlling PCB panel 23 and a drive power supply 24 inside.

The PCB panel 23 is disposed with a microprocessor 25, a training function selection module 26, a MP3 module 27 and a buzzer 28, wherein the microprocessor 25 is in electrical connection with the drive power supply 24, as well as the training function selection module 26 and the MP3 module 27 respectively, and the buzzer 28 is in electrical connection with the MP3 module 28.

It needs to be noted that, the training function selection module can adjust training modes, specifically, comprising selecting or switching the intraocular and extraocular muscle training modes, as well as increasing or reducing the training speed, so as to realize the adjustment of training difficulty; the microprocessor is used for receiving electrical signals from the training function selection module, so as to transmit a start signal to the intraocular muscle exercise bar or the extraocular muscle exercise light panel to lighten the LED guiding color lights or the LED guiding lights under corresponding modes; what's more, the microprocessor is also provided with a timing function to ensure a training time under each mode, so that when the preset training time is up, it can transmit electrical signals to the buzzer which sounds to remind of a training end.

Figure 4:
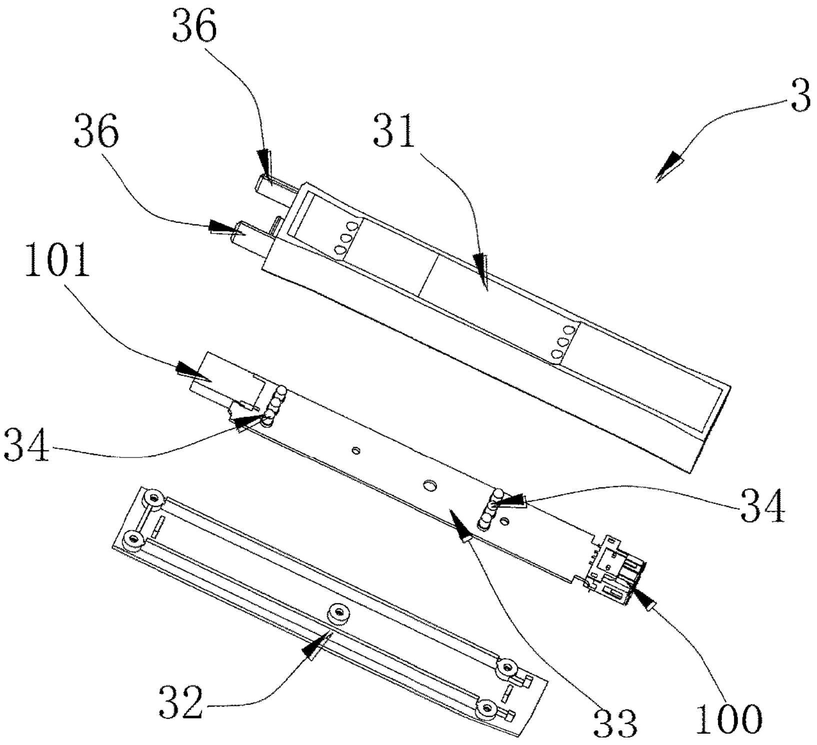
FIG. 4 is a structural diagram of the intraocular muscle exercise bar components shown in FIG. 1.

As shown in FIG. 4 and FIG. 5, the intraocular muscle exercise bar is connected via the several intraocular muscle exercise bar components 3, the shell of which is composed of an upper cover 31 and a lower cover 32 of the intraocular muscle exercise bar, with an intraocular muscle exercise light panel 33 disposed inside; the intraocular muscle exercise light panel 33 is arranged with at least a set of LED guiding color lights 34 on it, with its front and back ends disposed with an electrical connection port 100 and an electrical connection socket 101 respectively, and the several intraocular muscle exercise bar components 3 are connected in turn via the electrical connection port 100 or the electrical connection socket 101 and can continue to extend.

It also comprises diopter correcting lenses 14, as well as an extraocular muscle exercise light panel 4 disposed with several LED guiding lights 41 on it, in the ocular head 1; preferably, the number of the LED guiding lights provided in the present invention is eight.

As a preferable technical solution, it needs to be noted that, the intraocular muscle exercise bar consists of five to ten intraocular muscle exercise bar components, and each of the intraocular muscle exercise bar components is provided with two sets of vertically arranged LED guiding color lights with each set having three, wherein the colors of the LED guiding color lights include but are not limited to red, yellow or green light.

As a preferable technical solution, it needs to be noted that, both the electrical connection port and the electrical connection socket used between the ocular head and the control device and the intraocular muscle exercise bar components of the present invention are USB ports.

Figure 6:
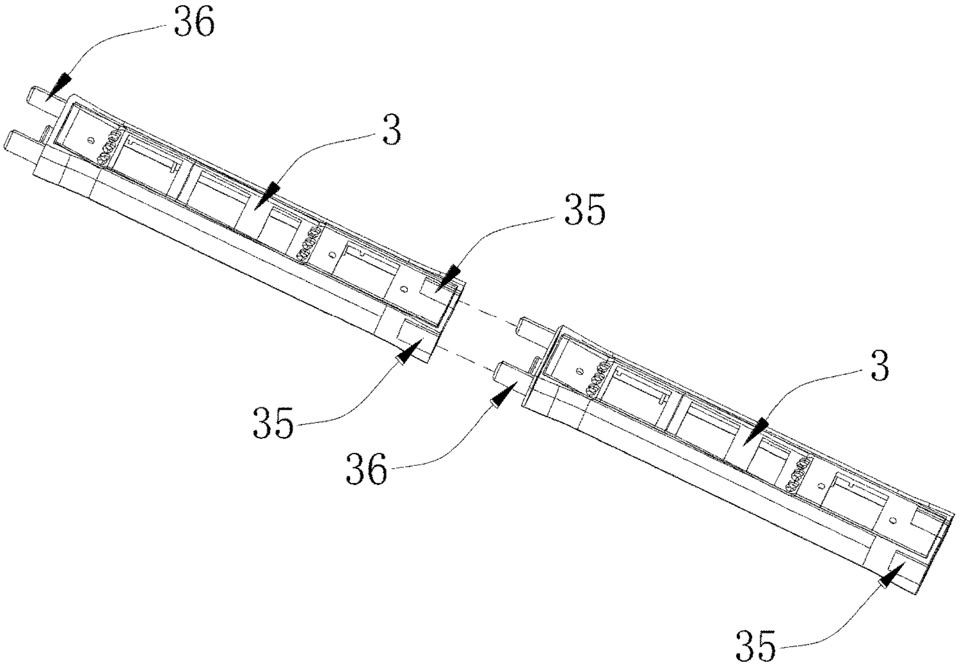
FIG. 6 is a connection structural diagram of the front-and-back intraocular muscle exercise bar components shown in FIG. 4.
Figure 7:
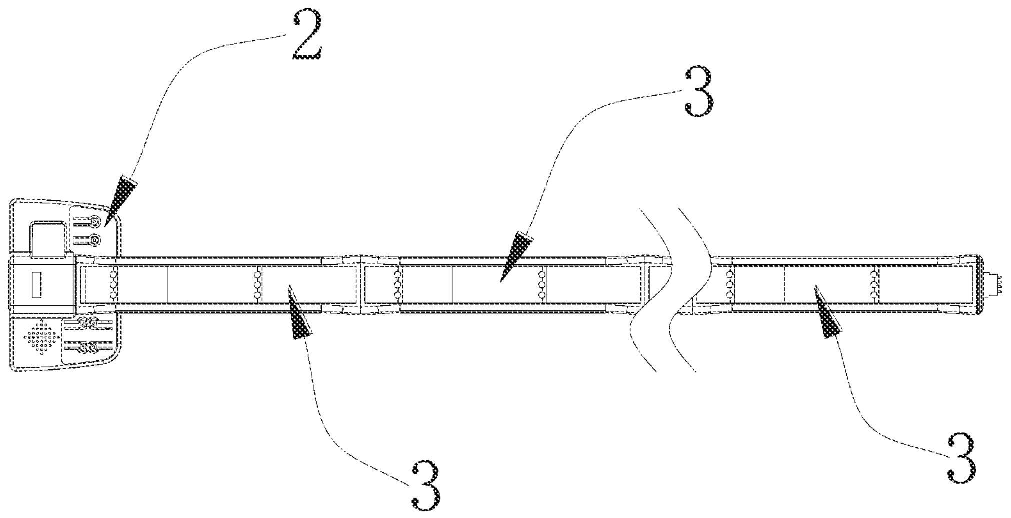
FIG. 7 is another embodiment of the present invention.

As shown in FIG. 4 and FIG. 6, to prevent the disjunction of the several intraocular muscle exercise bar components in connection, the front end of the intraocular muscle exercise bar components 3 is arranged with a groove 35, with its back end disposed with a flange 36 matched with the groove 35; as shown in FIG. 7, when the several intraocular muscle exercise bar components 3 are assembled for using, the flange 36 of the front intraocular muscle exercise bar component 3 is inserted into the groove 35 of the back intraocular muscle exercise bar component 3, which not only realizes extension, but also enhances the stability of the connection between individual components.

It needs to be further noted that the front end of the control device is disposed with the groove matched with the flange.

It needs to be further noted that positions of the several LED guiding lights arranged on the extraocular muscle exercise light panel shall be in correspondence with positions at the periphery of users' eyes.

As a preferable technical solution, as shown in FIG. 5, the back shell 13 of the ocular head is also disposed with a fixing band 200 designed for users to wear.

As a preferable technical solution, as shown in FIG. 3, to further relax users during training, the control device is also disposed with the MP3 module and the buzzer in electrical connection, aiming at making users more relaxed in music during the intraocular and extraocular muscle training in this way. To ensure the quality in use, of course, the buzzer sounds to remind of training end first, when the training time is up.

To meet different needs, the present invention also offers a variety of embodiments below, which however are not intended to limit the present invention:

As an embodiment, as shown in FIG. 7, the present invention is an intelligent intraocular muscle sensitivity exercise training instrument consisting of the control device 2 and the intraocular muscle exercise bar in electrical connection with the control device 2;

as shown in FIG. 2 and FIG. 3, consisting of its upper cover 21 and its lower cover 22, the shell of the control device 2 is disposed with a controlling PCB panel 23 and a drive power supply 24 inside;

the PCB panel 23 is disposed with a microprocessor 25, a training function selection module 26, a MP3 module 27 and a buzzer 28, wherein the microprocessor 25 is in electrical connection with the drive power supply 24, as well as the training function selection module 26 and the MP3 module 27 respectively, and the buzzer 28 is in electrical connection with the MP3 module 28.

It needs to be noted that, the training function selection module can adjust training modes, specifically, comprising selecting or switching the intraocular muscle training modes, as well as increasing or reducing the training speed, so as to realize the adjustment of training difficulty; the microprocessor is used for receiving electrical signals from the training function selection module, so as to transmit a start signal to the intraocular muscle exercise bar to lighten the LED guiding color lights under corresponding modes; what's more, the microprocessor is also provided with a timing function to ensure a training time under each mode, so that when the preset training time is up, it can transmit electrical signals to the buzzer which sounds to remind of a training end.

As shown in FIGS. 4 and 5, the intraocular muscle exercise bar is connected via the several intraocular muscle exercise bar components 3, the shell of which is composed of an upper cover 31 and a lower cover 32 of the intraocular muscle exercise bar, with an intraocular muscle exercise light panel 33 disposed inside; the intraocular muscle exercise light panel 33 is arranged with at least a set of LED guiding color lights 34 on it, with its front and back ends disposed with an electrical connection port 100 and an electrical connection socket 101 respectively, and the several intraocular muscle exercise bar components 3 are connected in turn via the electrical connection port 100 or the electrical connection socket 101 and can continue to extend;

As a preferable technical solution, it needs to be noted that, the intraocular muscle exercise bar consists of five to ten intraocular muscle exercise bar components, and each of the intraocular muscle exercise bar components is provided with two sets of vertically arranged LED guiding color lights with each set having three, wherein the colors of the LED guiding color lights include but are not limited to red, yellow or green light.

As a preferable technical solution, it needs to be noted that, both the electrical connection port and the electrical connection socket used between the control device and the intraocular muscle exercise bar components in the embodiment are USB ports.

As shown in FIGS. 4 and 6, to prevent the disjunction of the several intraocular muscle exercise bar components in connection, the front end of the intraocular muscle exercise bar components 3 is arranged with a groove 35, with its back end disposed with a flange 36 matched with the groove 35; as shown in FIG. 7, when the several intraocular muscle exercise bar components 3 are assembled for using, the flange 36 of the front intraocular muscle exercise bar component 3 is inserted into the groove 35 of the back intraocular muscle exercise bar component 3, which not only realizes extension, but also enhances the stability of the connection between individual components.

It needs to be further noted that the front end of the control device is disposed with the groove matched with the flange.

As a preferable technical solution, as shown in FIG. 3, to further relax users during training, the control device is also disposed with the MP3 module and the buzzer in electrical connection, aiming at making users more relaxed in music during the intraocular muscle training in this way. To ensure the quality in use, however, the buzzer sounds to remind of training end first, when the training time is up.

Figure 8:
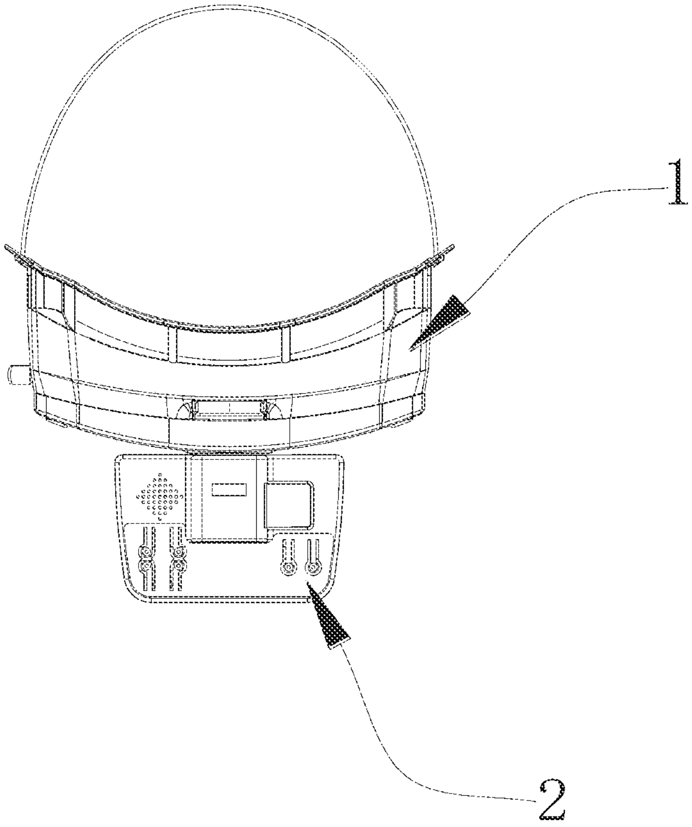
FIG. 8 is also another embodiment of the present invention.

As another embodiment, as shown in FIG. 8, the present invention is an intelligent extraocular muscle sensitivity exercise training instrument which is disposed with an ocular head 1 consisting of a front shell 11, a middle shell 12 and a back shell 13, and a control device 2 electrically connected to the ocular head 1;

as shown in FIGS. 2 and 3, consisting of its upper cover 21 and its lower cover 22, the shell of the control device 2 is disposed with a controlling PCB panel and a drive power supply 24 inside;

the PCB panel 23 is disposed with a microprocessor 25, a training function selection module 26, a MP3 module 27 and a buzzer 28, wherein the microprocessor 25 is in electrical connection with the drive power supply 24, as well as the training function selection module 26 and the MP3 module 27 respectively, and the buzzer 28 is in electrical connection with the MP3 module 28.

It needs to be noted that, the training function selection module can adjust training modes, specifically, comprising selecting or switching the extraocular muscle training modes, as well as increasing or reducing the training speed, so as to realize the adjustment of training difficulty; the microprocessor is used for receiving electrical signals from the training function selection module, so as to transmit a start signal to the extraocular muscle exercise light panel to lighten the LED guiding lights under corresponding modes; secondly, the microprocessor is also provided with a timing function to ensure a training time under each mode, so that when the preset training time is up, it can transmit electrical signals to the buzzer which sounds to remind of a training end.

It also comprises diopter correcting lenses 14, as well as an extraocular muscle exercise light panel 4 disposed with several LED guiding lights 41 on it, in the ocular head 1; preferably, the number of the LED guiding lights provided in the present invention is eight.

As a preferable technical solution, it needs to be noted that, both the electrical connection port and the electrical connection socket used between the ocular head and the control device of the present invention are USB ports.

It needs to be further noted that positions of the several LED guiding lights arranged on the extraocular muscle exercise light panel shall be in correspondence with positions at the periphery of users' eyes.

As a preferable technical solution, as shown in FIG. 5, the back shell 13 of the ocular head is also disposed with a fixing band 200 designed for users to wear.

As a preferable technical solution, as shown in FIG. 3, to further relax users during training, the control device is also disposed with the MP3 module and the buzzer in electrical connection, aiming at making users more relaxed in music during the extraocular muscle training in this way. To ensure the quality in use, however, the buzzer sounds to remind of training end first, when the training time is up.

Also as another embodiment, comprising the ocular head, the control device and the intraocular muscle exercise bar simultaneously, its structure is equal to the basic technical solution of the present invention, with the extraocular muscle exercise light panel removed from the basic technical solution however; only designed for intraocular training, the embodiment is not only provided with a function of diopter correcting lenses thanks to the ocular head disposed as well, but also allows users to wear it directly on head thus to bring more convenience to them.

Based on the structure of the above-mentioned training instrument, the present invention also provides the following training method:

a method using the intelligent intraocular and extraocular muscle sensitivity exercise training instrument for training, and the training method comprises:

S1, insert the control device into the ocular head;

S2, keep the intraocular muscle exercise bar components in front-and-back insert connection to reach the length required by users;

S3, insert the completely connected intraocular muscle exercise bar into the control device, so that users can wear the ocular head onto their eyes;

S4, turn on the power supply, and use the control device to adjust the training function selection module according to different needs, so as to trigger the LED guiding color lights or the LED guiding lights arranged on the intraocular muscle exercise bar or the extraocular muscle exercise light panel to start, thus to realize various training modes;

S5, when the training is completed, execute reverse steps of S1-S3 to separate and collect the ocular head, the control device and the intraocular muscle exercise bar components.

It needs to be noted that, the intraocular muscle training modes comprise:

“ ”-shaped single LED guiding color light cycle mode: LED guiding color lights are lightened one-by-one transversely from the first one at the frontmost end, until the last LED guiding color light is lightened, then the lights continue to be lightened one-by-one along a vertical direction and repeat the cycle, and stop five minutes later when a buzzer sounds;

whole-set cycle mode: taking a set of LED guiding color lights as a unit, the light sets are lightened one-by-one from the first one at the frontmost end to the last one, then repeat the cycle, and stop five minutes later when a buzzer sounds;

“ ”-shaped single LED guiding color light cycle mode: LED guiding color lights are lightened one-by-one transversely from the first one at the frontmost end, then repeat the cycle, and stop five minutes later when a buzzer sounds;

mixed mode: the three modes mentioned above appear repeatedly, and stop five minutes later when a buzzer sounds.

It needs to be noted that, the extraocular muscle training modes comprise:

Random cycle mode: LED guiding lights not adjacent to each other flash one-by-one cyclically in a random lightening way;

clockwise or anticlockwise cycle mode: LED guiding lights flash cyclically in a clockwise or anticlockwise direction;

flash mode: LED guiding lights at both left and right sides are lightened simultaneously and flash cyclically.

Embodiment 1

The ocular head is connected to the control device, and then the intraocular muscle exercise bar components are connected one-by-one to form an intraocular muscle exercise bar, according to users' needs. Specifically, the flange of the posterior intraocular muscle exercise bar component is inserted into the groove of the prior intraocular muscle exercise bar component, and the USB port and the socket disposed inside are connected; then, several completely connected intraocular muscle exercise bars are connected to the control device, and whereafter the ocular head could be put onto a suitable position of head via the fixing band; after turning on the power supply and selecting various training modes, users gaze at the LED guiding color lights arranged on the intraocular muscle exercise bar or the LED guiding lights on the extraocular muscle exercise bar. Wherein when the intraocular muscle training mode is selected, optional modes include “ ”-shaped single LED guiding color light cycle mode, a whole-set cycle mode, a “ ”-shaped single LED guiding color light cycle mode and a mixed mode; in this embodiment, the intraocular muscle exercise bar consists of seven intraocular muscle exercise bar components, and each of the intraocular muscle exercise bar components is provided with two sets of vertically arranged LED guiding color lights with each set having three, wherein the LED guiding color lights on the front two components close to the control device give out red light, with those on the middle two components and the rear three components respectively giving out yellow light and green light.

Figure 9A:
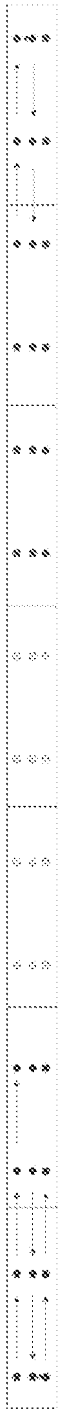
FIG. 9*a*-9*c* are diagrams of three intraocular muscle training modes of the present invention.

As shown in FIG. 9*a*, the “ ”-shaped single LED guiding color light cycle mode means that the LED guiding color lights are lightened one-by-one transversely from the first one at the frontmost end (closest to the control device) (it needs to be noted that, the prior LED guiding color light will go out when the posterior one is lightened), until the last LED guiding color light is lightened, then the lights continue to be lightened one-by-one along a vertical direction and repeat the cycle, and stop five minutes later when a buzzer sounds.

Figure 9B:

As shown in FIG. 9*b*, the whole-set cycle mode means that taking LED guiding color lights or a set of lights as an unit, the light sets are lightened one-by-one from the first one at the frontmost end (closest to the control device) (it needs to be noted that, the prior set of LED guiding color lights will go out when the posterior ones are lightened), and repeat the cycle, with the training under this mode ended five minutes later when a bell of the buzzer rings.

Figure 9C:

As shown in FIG. 9*c*, the “ ”-shaped single LED guiding color light cycle mode means that the LED guiding color lights are lightened one-by-one transversely from the first one at the frontmost end (closest to the control device) (it needs to be noted that, the prior LED guiding color light will go out when the posterior one is lightened), until the last LED guiding color light is lightened, then the lights continue to be lightened one-by-one along a vertical direction and repeat the cycle, and stop five minutes later when a buzzer sounds.

The mixed mode means that the three modes mentioned above repeat the cycle, with the training under this mode ended five minutes later when a bell of the buzzer rings.

It needs to be noted that, as a preferable embodiment, the intraocular muscle exercise bar consists of seven intraocular muscle exercise bar components, and each of the intraocular muscle exercise bar components is provided with two sets of vertically arranged LED guiding color lights with each set having three, wherein the LED guiding color rights on the front two components close to the control device give out red light, with those on the middle two components and the rear three components respectively giving out yellow light and green light.

Figure 10A:
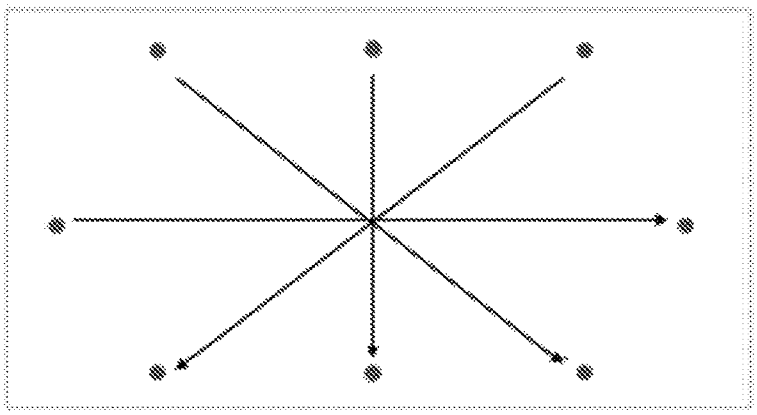
FIG. 10*a*-10*c* are diagrams of three extraocular muscle training modes of the present invention.
Figure 10B:
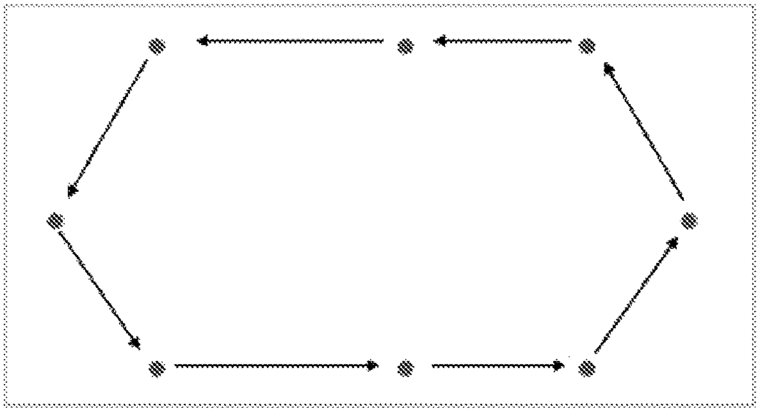
Figure 10C:
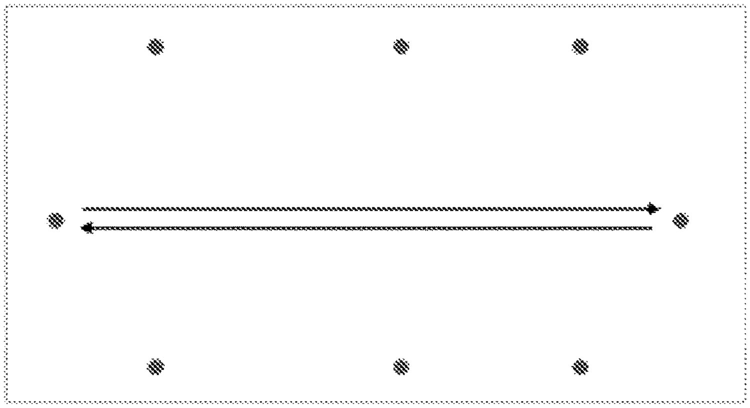

When the extraocular muscle training mode is selected, optional modes include a random cycle mode, a clockwise or anticlockwise cycle mode, and a flash mode;

as shown in FIG. 10*a*, the random cycle mode means that LED guiding lights not adjacent to each other flash one-by-one cyclically in a random lightening way;

as shown in FIG. 10*b*, the clockwise or anticlockwise cycle mode means LED guiding lights flash cyclically in a clockwise or anticlockwise direction;

as shown in FIG. 10*c*, the flash mode means that LED guiding lights at both left and right sides are lightened simultaneously and flash cyclically.

It needs to be noted that, the prior LED guiding light will go out when the posterior one is lightened under the three modes mentioned above.

At last, catering to different users, the training function selection module of the present invention is also provided with a high/low speed regulating function for adjustment of training difficulty; besides, it is also added with a MP3 playing function, not only keeping users more relaxed but also making the training less boring.

Embodiment 2

The structure and training method of this embodiment is basically consistent with Embodiment 1, only without the ocular head, so users just need to connect the control device to the intraocular muscle exercise bar and put it on a desk or a platform for training under the intraocular muscle training mode.

Embodiment 3

The structure and training method of this embodiment is basically consistent with Embodiment 1, only without the intraocular muscle exercise bar, so users just need to connect the ocular head to the control device and wear it on head for training under the extraocular muscle training mode.

Embodiment 4

The structure and training method of this embodiment is basically consistent with Embodiment 1, only without the extraocular muscle exercise light panel disposed in the ocular head, so users just need to connect the ocular head, the control device and the intraocular muscle exercise bar together and wear it on head for training under the intraocular muscle training mode.

The present invention is convenient to take along or install thanks to its structure. The LED guiding color lights with various cycle modes are arranged on the intraocular muscle exercise bar consisting of several intraocular muscle exercise bar components, which are actually equal to an intelligent sighting mark free of manual intervention; meanwhile, the present invention also integrates both intraocular and extraocular muscle training to enable free combination according to users' needs, and furthermore, the USB port is added to make the connection of the present invention more convenient and simple for different groups of people to use.

For those practitioners skilled in this field, a variety of corresponding modifications and variations can be made on the basis of the technical solutions and the concept of the present invention mentioned above. However, all the modifications and variations shall be covered in the protection scope of the Claims of the present invention.

What is claimed is:

1. An intelligent intraocular and extraocular muscle sensitivity exercise training instrument, characterized in that the training instrument is disposed with an ocular head consisting of a front shell, a middle shell and a back shell, and a control device electrically connected to the ocular head, as well as an intraocular muscle exercise bar electrically connected to the control device;

wherein the control device comprises a drive power supply, a microprocessor, a training function selection module, a MP3 module and a buzzer: the microprocessor is in electrical connection with the drive power supply, as well as the training function selection module and the MP3 module respectively, and the buzzer is in electrical connection with the MP3 module;

the intraocular muscle exercise bar is connected via several intraocular muscle exercise bar components, the shell of which is composed of an upper cover and a lower cover of the intraocular muscle exercise bar, with an intraocular muscle exercise light panel disposed inside; the intraocular muscle exercise light panel is arranged with at least a set of LED guiding color lights on it, with its front and back ends disposed with an electrical connection port and an electrical connection socket respectively, and the several intraocular muscle exercise bar components are connected in turn via the electrical connection port or the electrical connection socket;

it also comprises diopter correcting lenses, as well as an extraocular muscle exercise light panel disposed with several LED guiding lights on it, in the ocular head.

2. The intelligent intraocular and extraocular muscle sensitivity exercise training instrument of claim 1, characterized in that the front end of the intraocular muscle exercise bar components is arranged with a groove, with its back end disposed with a flange matched with the groove; when the several intraocular muscle exercise bar components need to be assembled for using, the flange of the prior intraocular muscle exercise bar component is inserted into the groove of the posterior intraocular muscle exercise bar component.

3. The intelligent intraocular and extraocular muscle sensitivity exercise training instrument of claim 1 or 2, characterized in that the intraocular muscle exercise bar consists of five to ten intraocular muscle exercise bar components, and each of the intraocular muscle exercise bar components is provided with two sets of vertically arranged LED guiding color lights with each set having three, wherein the colors of the LED guiding color lights include but are not limited to red, yellow or green light.

4. The intelligent intraocular and extraocular muscle sensitivity exercise training instrument of claim 2, characterized in that the front end of the control device is disposed with the groove matched with the flange.

5. The intelligent intraocular and extraocular muscle sensitivity exercise training instrument of claim 1, characterized in that positions of the several LED guiding lights arranged on the extraocular muscle exercise light panel shall be in correspondence with positions at the periphery of users' eyes.

6. The intelligent intraocular and extraocular muscle sensitivity exercise training instrument of claim 1, characterized in that both the electrical connection port and the electrical connection socket are USB ports.

7. The intelligent intraocular and extraocular muscle sensitivity exercise training instrument of claim 1, characterized in that the back shell of the ocular head is also disposed with a fixing band designed for users to wear.

8. A method using the intelligent intraocular and extraocular muscle sensitivity exercise training instrument of claim 1 for training, characterized in that the training method comprises:

S1, insert the control device into the ocular head;

S2, keep the intraocular muscle exercise bar components in front and-back insert connection to reach the length required by users;

S3, insert the completely connected intraocular muscle exercise bar into the control device, so that users can wear the ocular head around their eyes;

S4, turn on the power supply, and use the control device to adjust the training function selection module according to different needs, so as to trigger the LED guiding color lights or the LED guiding lights arranged on the intraocular muscle exercise bar or the extraocular muscle exercise light panel to start, thus to realize various training modes;

S5, when the training is completed, execute reverse steps of S1-S3 to separate and collect the ocular head, the control device and the intraocular muscle exercise bar components.

9. The training method as claimed in claim 8, characterized in that the intraocular muscle training mode comprises:

"己"-shaped single LED guiding color light cycle mode: LED guiding color lights are lightened one-by-one transversely from the first one at the frontmost end, until the last LED guiding color light is lightened, then the lights continue to be lightened one-by-one along a vertical direction and repeat the cycle, and stop five minutes later when a buzzer sound;

whole-set cycle mode: taking a set of LED guiding color lights as a unit, the light sets are lightened one-by-one from the first one at the frontmost end to the last one, then repeat the cycle, and stop five minutes later when a buzzer sounds;

"ᒪᒋ"-shaped single LED guiding color light cycle mode: LED guiding color lights are lightened one-by-one transversely from the first one at the frontmost end, then repeat the cycle, and stop five minutes later when a buzzer sounds;

mixed mode: the three modes mentioned above appear repeatedly, and stop five minutes later when a buzzer sounds.

10. The training method of claim 8, characterized in that the extraocular muscle training mode comprises:

random cycle mode: LED guiding lights not adjacent to each other flash one by one cyclically in a random lightening way;

clockwise or anticlockwise cycle mode: LED guiding lights flash cyclically in a clockwise or anticlockwise direction;

flash mode: LED guiding lights at both left and right sides are lightened simultaneously and flash cyclically.

* * * * *